United States Patent
Owen et al.

(10) Patent No.: US 7,148,963 B2
(45) Date of Patent: Dec. 12, 2006

(54) LARGE-COLLECTION-AREA OPTICAL PROBE

(75) Inventors: Harry Owen, Ann Arbor, MI (US); David J. Strachan, Timonium, MD (US); Joseph B. Slater, Dexter, MI (US); James M. Tedesco, Livonia, MI (US)

(73) Assignee: Kaiser Optical Systems, Ann Arbor, MI (US)

( * ) Notice: Subject to any disclaimer, the term of this patent is extended or adjusted under 35 U.S.C. 154(b) by 0 days.

(21) Appl. No.: 11/007,969

(22) Filed: Dec. 9, 2004

(65) Prior Publication Data

US 2005/0140973 A1    Jun. 30, 2005

Related U.S. Application Data

(60) Provisional application No. 60/528,577, filed on Dec. 10, 2003.

(51) Int. Cl.
    *G01N 21/64* (2006.01)
(52) U.S. Cl. ........................ 356/301; 356/317
(58) Field of Classification Search ............... 356/301, 356/317, 318, 417
    See application file for complete search history.

(56) References Cited

U.S. PATENT DOCUMENTS

| | | | |
|---|---|---|---|
| 4,573,761 A | | 3/1986 | McLachlan et al. ..... 350/96.24 |
| 5,112,127 A | * | 5/1992 | Carrabba et al. ......... 356/301 |
| 5,842,995 A | * | 12/1998 | Mahadevan-Jansen et al. ..... 600/473 |
| 6,483,581 B1 | * | 11/2002 | Ben-Amotz et al. ...... 356/301 |
| 6,486,948 B1 | * | 11/2002 | Zeng ......................... 356/301 |
| 6,795,177 B1 | * | 9/2004 | Doyle ....................... 356/301 |
| 6,809,812 B1 | * | 10/2004 | Yin ............................ 356/301 |
| 6,809,813 B1 | * | 10/2004 | Bennett et al. ............ 356/301 |

OTHER PUBLICATIONS

Zhiwei Huang, Haishen Zeng, Iltefat Hamzavi, David I. McLean, and Harvey Lui, "Rapid near-infrared Raman spectroscopy system for real-time in vivo skin measurements," Optic Letters, vol. 26, No. 22, Nov. 15, 2001.

* cited by examiner

*Primary Examiner*—Layla G. Lauchman
(74) *Attorney, Agent, or Firm*—Gifford, Krass, Groh, Sprinkle, Anderson & Citkowski, PC

(57) ABSTRACT

A compact Raman/fluorescence probe is capable of collecting spectra from a relatively large spot size as compared to traditional confocal Raman probes. The inventive probe collects spectra from an area or 1 mm or greater, preferably 3–12 mm or more, compared to current instruments which utilize spot sizes on the order of 2–60 microns. The larger spot size facilitates the collection of statistically useful data from inhomogeneous and laser-sensitive samples, among other applications. Potential pharmaceutical applications include tablet dosage level measurements, as well as online and at-line quality-control (QC) monitoring opportunities. Other applications include tablet identification as a forensic tool to identify counterfeit pharmaceutical products; granulation and blend uniformity for improved formulation via better process understanding, and reactor cleanliness validation.

23 Claims, 1 Drawing Sheet

LARGE-COLLECTION-AREA OPTICAL PROBE

REFERENCE TO RELATED APPLICATION

This application claims priority from U.S. Provisional Patent Application Ser. No. 60/528,577, filed Dec. 10, 2003, the entire content of which is incorporated herein by reference.

FIELD OF THE INVENTION

This invention relates generally to optical measurement probes and, in particular, to Raman/fluorescence probe which is capable of collecting spectra from a large spot size.

BACKGROUND OF THE INVENTION

Fiber-optic probes make it possible to collect optical information such as Raman spectra without having to place the material being characterized inside a spectrometer housing. Such probes therefore simplify the interfacing of spectroscopic systems to samples under investigation, and allow analytical instruments to be located remotely from environments in need of spectroscopic monitoring.

The first remote fiber optic probes for Raman spectroscopy were reported by the McCreery group in the early 1980's. Their design used a single optical fiber to deliver laser light to the sample and a single optical fiber to collect light scattered by the sample. More specifically, divergent laser light from the laser delivery fiber was used to illuminate the sample, and light scattered from the sample within the acceptance cone of the collection fiber was transmitted back to the spectrograph. The efficiency of exciting and collecting Raman photons from any individual point in the sample was poor, but the integrated Raman intensity over the unusually large analysis volume compared favorably with the more traditional imaged illumination and collection configurations.

Several improvements to the McCreery Raman probe have more recently been reported. Instead of using just one collection fiber, multiple fibers have been used to increase the collection efficiency. For example, 6 fibers, each having the same diameter as the excitation fiber, may be grouped around the excitation fiber to form a single circular layer, as shown in U.S. Pat. No. 4,573,761. The performance of the McCreery type probe can also be modified for improved collection efficiency and/or working distance by changing the overlap between the emission cone of the excitation fiber and the collection cones of the collection fibers. An early realization of this idea, as disclosed in U.S. Pat. No. 4,573,761, angled the collection fibers such that their optic axes intersected the optic axis of the illumination fiber. This increased the overlap of the excitation and collection cones close to the tip of the fiber probe, where the excitation and collection of Raman photons was most efficient.

One further variation of the McCreery probe design is to use collection fibers having a different diameter than the excitation fiber. This additional variable is useful for changing the working distance of the probe and the fiber coupling to the spectrograph. However, one disadvantage of existing probes in their relatively small spot size. The large intensity of the small spot limits applications, often requiring scanning to cover a larger sample area. The high intensity of the small spot also precludes certain temperature-sensitive applications, including direct human contact. One of the most significant limitations of existing bundle probe designs is that they are not confocal, there is not complete overlap of the excitation light with the collection aperture.

SUMMARY OF THE INVENTION

This invention resides in a compact Raman/Fluorescence probe which is capable of collecting spectra from a relatively large spot size, confocally as compared to traditional Raman probes. In the preferred embodiment, the inventive probe collects spectra from an urea of 1 mm or greater, preferably 3–12 mm or more, as compared to current instruments which utilize spot sizes on the order of 2–60 microns. The fact that the large data collection area is confocal with the excitation light vastly improves the signal efficiency or the overall probe.

The larger spot size facilitates the collection of statistically useful data from inhomogeneous and laser-sensitive samples, among other applications. Potential pharmaceutical applications include tablet dosage level measurements, as well as online and at-line quality-control (QC) monitoring opportunities. Other applications include tablet identification as a forensic tool to identify counterfeit pharmaceutical products; granulation and blend uniformity for improved formulation via better process understanding; and reactor cleanliness validation, since cleaning reactors between the manufacture of different drug substances is very time consuming and therefore expensive.

Another area of interest is using the lower laser energy density provided by expanding the laser to up to 10 mm or more to analyze skin and the effects of cosmetics on skin without causing damage to the skin. The probe conforms to the ANSI standards and is therefore skin safe.

DETAILED DESCRIPTION OF THE INVENTION

Figure 1:
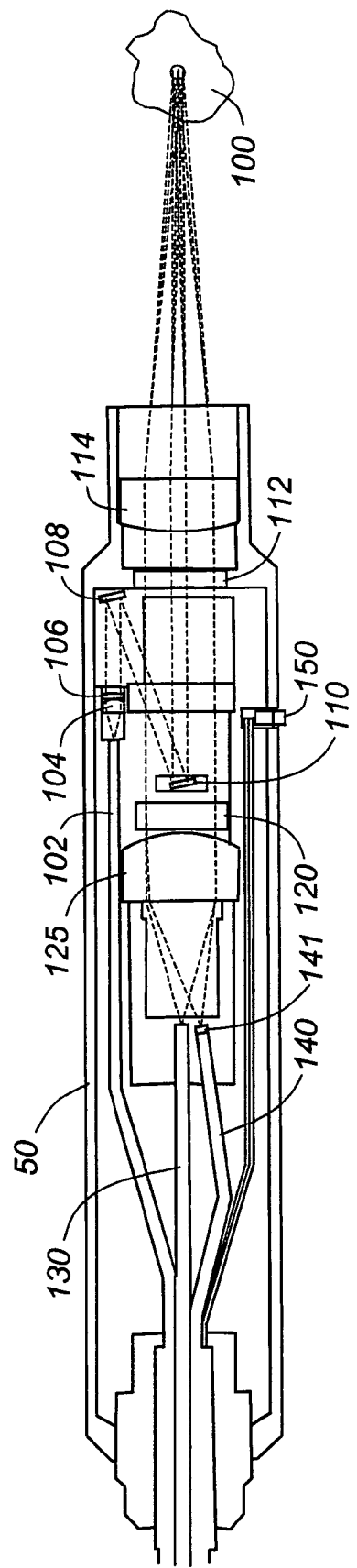
FIG. 1 is a cross-sectional representation of a probe constructed in accordance with this invention.

Making reference to FIG. 1, a probe according to the invention includes a housing 50 including various optical elements described in further detail below. An optional indicator lamp is shown at 150. This is preferably electrically driven from a remote source to function as a cable breakage indicator as well.

Excitation light passing through fiber 102 is collimated by a short-focal-length lens 104 and passed through a bandpass filter 106 to remove fiber noise. From there the excitation light is reflected by a mirror 108 to a combiner 110, preferably a small wavelength-sensitive reflector (i.e., a reflective edge filter). The light then passes through an exit window 112, and is imaged by the sample lens 114 onto a sample 100.

Raman/fluorescence signal light and reflected unshifted excitation light passes back through the sample lens 114 and through a notch filter 120. The combiner 110 occupies only a small amount of the return aperture and thus has little effect on the collected light. The notch filter 120 removes the unshifted excitation light, leaving only the signal light to be focused onto the collection fiber bundle 130, which then connects to a spectrograph (not shown) for analysis.

An import aspect of the invention involves a pronounced asymmetric magnification ration between excitation and collection. In contrast to existing probe designs, wherein the ratio of the excitation image to the collection image at the target is less than 2:1 if not substantially the same, this invention utilizes a ratio of 2:1 or greater, up to 6:1 or higher in the preferred embodiments. To accomplish this, the focal length of the sample optic, which transmits a counter-propagating excitation/collection beam, is two to six times greater than the focal length of the excitation optic used to collimate the excitation beam, resulting in a highly magnified excitation image. In addition, the ratio of the focal length to the of the collection optic to the focal length of the excitation optic matches the ratio of the diameter of the excitation fiber(s) to the diameter of the collection fiber(s), so that the image diameters of the two fibers are approximately the same at the sample.

Since the focal length of the excitation lens 104 is small compared to that of the sample lens 114, the image of the excitation fiber is highly magnified. The focal length of the collection lens 125, however, is comparable to the sample lens 114 and thus is less magnified. However, since the ratio of the collection and excitation lenses preferably matches the ratio of the diameter of the excitation fiber to the collection bundle diameter, the image diameters of the two fibers are approximately the same at the sample, optimizing signal-generation capacity.

Although single and multiple fibers may be used for either the excitation or collection paths, in the preferred embodiment a single excitation fiber is used in conjunction with a bundle of collection fibers (typically 50, more or less). The diameter of the excitation fiber may vary, which dictates the ratio of the magnification of the excitation image to the collection image. Excitation fibers in the range of 200 microns to 1 mm are preferred.

The collection fiber bundle preferably has an input end with the fibers arranged in a circle and an output end with the fibers are arranged in a line so that the resolution inherent in the use of small individual fibers is maintained at the spectrograph. The use of a collection fiber bundle is also useful in various analysis situations, including uniformity measurements. For example, with respect to pharmaceutical applications, the signals across a group or all of the fibers may be measured to determine an average. While the average may be useful for certain information such as active ingredient dosage, individual or smaller groups of fibers may be sub-sampled to determine the distribution of constituents such as lubricants, fillers, binders, disintegrants, and other active or inactive ingredients. The uniformity of substances such as disintegrants is particularly useful, since an uneven distribution may affect dissolution as a function of time.

In order to function optimally, the fibers in the collection bundle are calibrated. This is done through the use of a calibration fiber 140 carrying neon light or another calibration signal. This light illuminates a diffuser 141 disposed at the tip of fiber 140. Light from the diffuser 141 is collimated by the collection lens, which is partially reflected by the notch filter such that it forms an image of the diffuser on the collection fiber bundle.

We claim:

1. An optical measurement probe, comprising:
    one or more excitation fibers for carrying excitation light to a sample under investigation;
    one or more collection fibers for carrying Raman or fluorescence spectra; and
    a plurality of stationary optical elements which cooperate to facilitate the collection of the spectra over a sample spot confocal with the excitation light having a size of 3–12 mm or greater.

2. The optical measurement probe of claim 1, wherein the optical elements include:
    an excitation lens for collimating the excitation light;
    a sample lens for focusing the excitation light onto the sample and for collimating light received from the sample; and
    wherein the focal length of the excitation lens is small compared to the focal length of the sample lens such that the image of the excitation fiber is highly magnified at the sample.

3. The optical measurement probe of claim 2, wherein the ratio of the focal length of the sample lens to the focal length of the excitation lens is 2:1 or greater.

4. The optical measurement probe of claim 1, further including:
    a bundle of collection fibers;
    an excitation lens for collimating the excitation light;
    a collection lens for focusing the Raman or fluorescence spectra onto the bundle of collection fibers; and
    wherein the ratio of the focal lengths of the collection and excitation lenses matches the ratio of the diameter of the excitation fiber to the collection bundle diameter such so that the image diameters of the two fibers are approximately the same at the sample.

5. The optical probe of claim 1, further including:
    a bundle of collection fibers; and
    wherein the bundle has an input end with the fibers arranged in a circle and an output end with the fibers are arranged in a line.

6. The optical measurement probe of claim 1, further including:
    a sample lens for focusing the excitation light on to the sample and for collimating light received from the sample;
    a collection lens for focusing the Raman or fluorescence spectra onto the collection fiber, and
    wherein the focal length of the collection lens is comparable to the focal length of the sample lens.

7. The optical measurement probe of claim 1, further including a fiber for carrying calibration light.

8. The optical measurement probe of claim 1, including a bundle of collection fibers.

9. The optical measurement probe of claim 1, including a single excitation fiber.

10. An optical measurement probe, comprising:
    one or more excitation fibers for carrying excitation light to a sample under investigation;
    an excitation lens for collimating the excitation light;
    a sample lens for focusing the excitation light onto the sample and for collimating light received from the sample;
    one or more collection fibers for carrying Raman or fluorescence spectra; and the focal length of the excitation lens being small compared to the focal length of the sample lens, such that the image of the excitation fiber is highly magnified at the sample, thereby facilitating the collection of the spectra over a sample spot size of 1 mm or greater.

11. The optical measurement probe of claim 10, wherein the ratio of the focal length of the sample lens in the focal length of the excitation lens is 2:1 or greater.

12. The optical measurement probe of claim 10, further including:
    a bundle of collection fibers;
    a collection lens for focusing the Raman or fluorescence spectra onto the bundle of collection fibers; and wherein the ratio of the focal lengths of the collection and excitation lenses matches the ratio of the diameter of the excitation fiber to the collection bundle diameter such so that the image diameters of the two fibers are approximately the same at the sample.

13. The optical probe of claim 12, further wherein the bundle has an input end with the fibers arranged in a circle and an output end with the fibers are arranged in a line.

14. The optical measurement probe of claim 10, further including:
   a sample lens for focusing the excitation light on to the sample and for collimating light received from the sample;
   a collection lens for focusing the Raman or fluorescence spectra onto the collection fiber; and
   wherein the focal length or the collection lens is comparable to the focal length of the sample lens.

15. The optical measurement probe of claim 10, further including a fiber for carrying calibration light.

16. The optical measurement probe of claim 10, including a single excitation fiber.

17. An optical measurement probe, comprising:
   one or more excitation fibers for carrying excitation light to a sample under investigation;
   an excitation lens for collimating the excitation light;
   a bundle of collection fibers collection fibers for carrying Raman or fluorescence spectra;
   a collection lens for focusing the Raman or fluorescence spectra onto the bundle of collection fibers; and
   wherein the ratio of the collection and excitation lenses matches the ratio of the diameter of the excitation fiber to the collection bundle diameter such so that the image diameters of the two fibers are approximately the same at the sample, thereby facilitating the collection of the spectra over sample spot size of 1 mm or greater.

18. The optical measurement probe of claim 17, further including:
   a sample lens for focusing the excitation light onto the sample and for collimating light received from the sample; and
   wherein the focal length of the excitation lens is small compared to the focal length of the sample lens such that the image of the excitation fiber is highly magnified at the sample.

19. The optical measurement probe of claim 18, wherein the ratio of the focal length of the sample lens to the focal length of the excitation lens is 2:1 or greater.

20. The optical probe of claim 17, wherein the bundle has an input end with the fibers arranged in a circle and an output end with the fibers are arranged in a line.

21. The optical measurement probe of claim 17, further including:
   a sample lens for focusing the excitation light on to the sample and for collimating light received from the sample;
   a collection lens for focusing the Raman or fluorescence spectra onto the collection fiber; and
   wherein the focal length of the collection lens is comparable to the focal length of the sample lens.

22. The optical measurement probe of claim 17, further including a fiber for carrying calibration light.

23. The optical measurement probe of claim 17, including a single excitation on fiber.

* * * * *

UNITED STATES PATENT AND TRADEMARK OFFICE
CERTIFICATE OF CORRECTION

| | | |
|---|---|---|
| PATENT NO. | : 7,148,963 B2 | Page 1 of 1 |
| APPLICATION NO. | : 11/007969 | |
| DATED | : December 12, 2006 | |
| INVENTOR(S) | : Harry Owen et al. | |

It is certified that error appears in the above-identified patent and that said Letters Patent is hereby corrected as shown below:

On the title page item (57), in the Abstract, line 4, replace "or" with --of--

Column 2, line 10, replace "urea" with --area--

Column 2, line 14, replace "or" with --of--

Column 4, line 28, delete "are"

Column 5, line 16, replace "or" with --of--

Column 6 , line 26, delete the second occurrence of "collection fibers"

Column 6, line 17, delete "are"

Column 6, line 31, delete "on"

Signed and Sealed this

Tenth Day of April, 2007

JON W. DUDAS
*Director of the United States Patent and Trademark Office*